United States Patent [19]

Yoshina, deceased et al.

[11] 4,126,625
[45] Nov. 21, 1978

[54] CERTAIN 5-SUBSTITUTED-3-METHYL-2-BENZOFURAN ACETIC ACIDS

[75] Inventors: Shigetaka Yoshina, deceased, late of Aichi, Japan; by Teruko Yoshina, legal heir, Nagoya, Japan; Tsutomu Kameyama, Nagoya, Japan; Yoshimasa Oiji, Sakai, Japan; Akira Kiyohara, Nishinomiya, Japan

[73] Assignee: Kyowa Hakko Kogyo Kabushiki Kaisha, Ohtemachi, Japan

[21] Appl. No.: 704,604

[22] Filed: Jul. 12, 1976

[30] Foreign Application Priority Data

Jul. 1, 1975 [JP] Japan .................................. 50-84997
Jul. 1, 1975 [JP] Japan .................................. 50-84998
Nov. 12, 1975 [GB] United Kingdom ............... 46749/75

[51] Int. Cl.$^2$ .......................................... C07D 307/80
[52] U.S. Cl. ................................. 260/346.22; 424/285
[58] Field of Search ................................. 260/346.2 R

[56] References Cited

U.S. PATENT DOCUMENTS 3,682,976  8/1972  Kaltenbronn et al. ....... 260/346.2 R
3,862,134  1/1975  Scherrer ....................... 260/346.2 R

OTHER PUBLICATIONS

Aurozo et al., Eur. J. Med. Chem.-Chimica Therapeutica, Mar.-Apr. 1975, vol. 10-No. 2, pp. 182-186.
Sila et al., Roczniki Chemii vol. 44, (1970), pp. 1319-1322.
Deohra et al., Chem. Ab. vol. 62 (1965) 7714c.

Primary Examiner—John D. Randolph
Assistant Examiner—Bernard Dentz
Attorney, Agent, or Firm—Wolder, Gross & Yavner

[57] ABSTRACT

This invention relates to certain derivatives of benzo (b) furylacetic acid, namely, 5-substituted-3-methyl-2-benzo(b)furylacetic acids having interesting pharmacological properties, in particular an antiphlogistic and analgesic activity.

5 Claims, No Drawings

CERTAIN 5-SUBSTITUTED-3-METHYL-2-BENZOFURAN ACETIC ACIDS

BACKGROUND OF THE INVENTION

Various antiphlogistic and analgesic agents are known but it is generally found that the antiphlogistic and analgesic agents conventionally used have a rather high toxicity and often induce various undesired side effects such as for example gastric lesions. There is thus a need for antiphlogistic and analgesic agents having a lower toxicity and no undesired side effects.

It is known that chloro-5-benzo(b)furyl-2 carboxylic acid, chloro-5-benzo(b)furyl-2-acetic acid, methoxy-5-benzo(b) furyl-2-acetic acid and a derivative of substituted β-(benzo(b)furyl-2) acrylic acid have a lower anti-inflammatory activity and a minor toxicity than phenylbutazone (Eur. J. Med. Chem. - Chimica Therapeutica, March-April 1975-10, N. 2, p. 182–186).

The present invention is concerned with the following 5-substituted-3-methyl-2-benzo(b) furylacetic acids of general formula

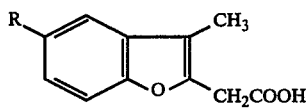

wherein R represents a hydrogen atom; an alkyl group containing 1 to 6 carbon atoms, e.g. a methyl, ethyl, n-propyl, isopropyl, n-butyl, sec-butyl, tert-butyl, n-pentyl or n-hexyl group; an alkoxy group containing 1 to 6 carbon atoms, e.g. a methoxy, ethoxy, n-propoxy or isopropoxy group; a cycloalkyl group containing 3 to 6 carbon atoms, e.g. a cyclopropyl, cyclobutyl, cyclopentyl or cyclohexyl group; a cycloalkoxy group containing 3 to 6 carbon atoms, e.g. a cyclopropoxy group; an alkenyl group containing 3 or 4 carbon atoms, e.g. a propenyl or 1-butenyl group; an alkenyloxy group containing 3 or 4 carbon atoms, e.g. a propenyloxy or isopropenyloxy group; a cyclohexenyloxy group; a phenyl group or a substituted phenyl group having the formula

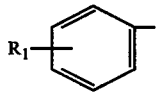

wherein $R_1$ represents a methoxy group; a halogen atom, e.g. a fluorine or chlorine atom; or an alkyl group containing 1 to 4 carbon atoms, e.g. a methyl, ethyl, propyl, n-butyl, sec-butyl or tert-butyl group; a phenoxy group; a benzyl group; a substituted benzyl group having the formula:

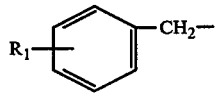

wherein $R_1$ is as defined above; a trifluoromethyl group; or a halogen atom, e.g. a fluorine, chlorine or bromine atom and phsyiologically acceptable salts thereof.

The present invention is further concerned with the discovery that the 5-substituted-3-methyl-2-benzo(b-)furylacetic acids of general formula (I) show antiphlogistic and analgesic activities.

Thus according to the present invention there are provided pharmaceutical compositions comprising as active ingredient a compound of formula (I) as hereinbefore defined or a physiologically acceptable salt thereof in association with a pharmaceutical carrier or excipient.

Among the derivatives of benzo (b) furylacetic acid represented by the formula (I), the derivatives where R is a hydrogen atom [Chem. Ber. 97, 3577 (1964)], a methyl radical [Rocz. Chem. 44, 1913 (1970)] and a chlorine atom [Indian Journal of Chem., 2, 456 (1964)] were previously known, although it was not known that these compounds had antiphlogistic and analgesic properties. The other compounds of general formula (I) are however new compounds and constitute a further feature of the present invention.

The preparations of the three known compounds, 3-methyl-2-benzo(b) furylacetic acid, 3,5-dimethyl-2-benzo(b)furylacetic acid and 5-chloro-3-methyl-2-benzo(b)furylacetic acid are described in the above indicated literature references. However, these preparations have disadvantages of complicated steps and a low yield.

The present invention is accordingly to provide processes for preparing the derivatives of benzo(b)furylacetic acid of the formula (I) with a high yield in a simple manner. According to the present invention, the derivatives of benzo(b)furylacetic acid represented by the formula (I) can be prepared by the process exemplified as follows:

(A) Process using as a starting material 3-methyl-2-cyanomethylbenzo(b) furan or 5-substituted derivatives thereof having the general formula (II)

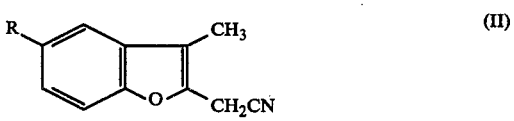

wherein R is as hereinbefore defined.

The compounds of general formula (I) can be prepared from the starting compound by hydrolysis in an aqueous medium in the presence of an acid or alkali.

Acids which are preferably used for this purpose are, for example, hydrochloric acid, sulfuric acid, phosphoric acid and para-toluenesulfonic acid. It is also possible to use a strongly acidic ion exchange resin.

Alkalies which are preferably used for this purpose are, for example, hydroxides of alkali metals and alkaline earth metals, e.g. sodium hydroxide, potassium hydroxide and calcium hydroxide.

The hydrolysis is preferably effected in the presence of a solvent, especially an organic solvent which does not react with the starting compound and which is miscible with water. Preferred organic solvents include, for example, dioxane, tetrahydrofuran, acetone, 2-methoxyethanol, 2-ethoxyethanol and lower alcohols, e.g. methanol, ethanol, n-propanol, isopropanol, n-butanol and tert-butanol. Advantageously the organic solvent is present in an amount of from ¼ to 4 times the volume of water. In the reaction, 0.01 mole to 1.0 mole, preferably 0.1 mole-0.5 mole, of the starting compound is used per one liter of the total solvent.

The reaction is usually carried out at a temperature within the range of from 50° to 100° C., preferably at about the boiling point of the organic solvent used. After completion of the hydrolysis, the reaction mixture is concentrated. If desired, the reaction mixture is treated with active charcoal prior to the concentration. The pH of the concentrated mixture is then adjusted to a pH of 2 with an acid, for example, hydrochloric acid or sulfuric acid, and is cooled to precipitate crude crystals. The crude crystals are then recrystalized from a suitable solvent, for example an aqueous solution of an alcohol to yield the purified final compound.

The starting compounds of general formula (II), 3-methyl-2-cyanomethylbenzo(b)furan and 5-substituted derivatives thereof, can be prepared, for example, by the process disclosed in DT-AS 1,203,277. They can also be prepared as follows:

Phenol or an appropriate p-substituted-phenol of formula

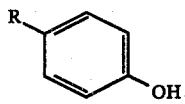

wherein R is as hereinbefore defined, is reacted with an equimolar amount of sodium hydroxide in an aqueous medium to give a sodium salt of phenol or the p-substituted phenol respectively which is then treated with ethyl α-chloracetoacetate to yield a compound of formula

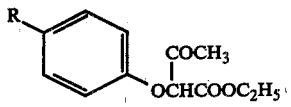

wherein R is as hereinbefore defined. The ethyl α-(phenoxy)acetoacetate or ethyl-α-(p-substituted-phenoxy) acetoacetate obtained is then subjected to ring-closure by treatment with concentrated sulfuric acid to give 3-methyl-2-ethoxycarbonylbenzo(b) furan or a 5-substituted derivative thereof of formula

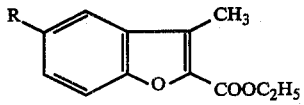

wherein R is as hereinbefore defined. The resultant compound is subjected to reduction with lithium aluminium hydride in an organic solvent, e.g. diethyl ether, to give 3-methyl-2-hydroxymethylbenzo(b)furan or a 5-substituted derivative thereof of formula

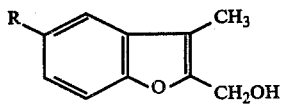

wherein R is as hereinbefore defined. This compound is then treated with thionyl chloride to give 3-methyl-2-chloromethylbenzo(b) furan or a 5-substituted derivative thereof of formula

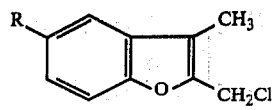

wherein R is as hereinbefore defined, which is then subjected to reaction with sodium cyanate to give 3-methyl-2-cyanomethylbenzo(b) furan or a 5-substituted derivative thereof of formula (II).

(B) Process using as a starting compound 3-methyl-2-acetylbenzo(b)furan or 5-substituted derivatives thereof having general formula (III)

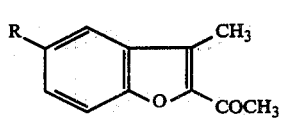

wherein R is as hereinbefore defined.

The starting compound, which can be obtained, for example, by the process described in Bull. Soc. Chim. Fr., 1970 (10), page 3601, is reacted with hydrogen sulfide or sulphur together with ammonia, a primary amine or a secondary amine in an aqueous solution or in an aqueous solution of organic solvent to obtain its thioamide.

Amines which may be used for this purpose include, for example, methylamine, pyridine, morpholin and the like.

The organic solvent which may be used for the reaction includes, for example, dioxane, piperidine and the like. It is also possible to use the amine as both the reaction material and the organic solvent. In the reaction, 0.01 mole to 2.0 mole, preferably 0.1 mole-1.5 moles of the starting compound is used per one liter of the total solvent. When morpholin is used as both the reaction material and the organic solvent, as for the amount of sulphur and morpholin, 1.3 to 1.7 moles, preferably 1.5 moles of both compounds are used per one mole of the starting material of general formula (III).

The reaction is preferably carried out at a temperature within the range of from 130° to 200° C. for about from 5 to 25 hours. After completion of the reaction, the reaction mixture is cooled to precipitate crystals of the thioamide. If desired, it is also possible to otain the thioamide with a better yield by concentrating the reaction mixture, removing the solvent and adding water.

The thus-obtained thioamide is subjected to the hydrolysis with a suitable acid or alkali to give the desired 5-substituted-3-methyl-2-benzo(b)furylacetic acid represented by general formula (I). The acids which may with advantage be used for this purpose are exemplified by hydrochloric acid, sulfuric acid, paratoluene-sulfonic acid and the like; and the alkalis which are preferably used for this purpose include for example hydroxides of alkali metals and alkaline earth metals such as sodium hydroxide, potassium hydroxide and calcium hydroxide. In the reaction, 0.01 mole to 1.0 mole, preferably 0.1 mole-0.5 mole of the starting compound is used per one liter of the total solvent.

The desired final product can be isolated for example in the following manner.

The reaction mixture containing the desired final product obtained by the hydrolysis is adjusted to a neutral pH for example with sodium carbonate and then washed with a suitable solvent such as for example benzene. After this, the water layer in the reaction solution is adjusted to an acidic pH 2, for example with a suitable dilute acid such as dilute hydrochloric acid, dilute sulfuric acid and the like to isolate the desired acid which is then extracted for example with ethylacetate and the like. After removal of water from the extract, the organic solvent of the extract is concentrated to obtain the desired crude product. The recrystalization is then carried out by the use of a suitable solvent such as, for example, an aqueous solution of alcohol, ethanol and the like.

Preferred physiologically acceptable salts of 3-methyl-2-benzo(b)furylacetic acid and the 5-substituted derivatives thereof of general formula (I) for incorporation into the pharmaceutical compositions according to the invention are, for example, the sodium, potassium, calcium and aluminium salts (obtained by reaction with the appropriate metal oxide or hydroxide) and also the physiologically acceptable non-toxic ammonium and amine salts (obtained by reaction with for example ammonia, diethylamine or triethanolamine).

The pharmaceutical compositions according to the present invention may with advantage be presented in a form suitable for internal or external administration, e.g. oral or topical administration, for example as tablets, granules, powders, capsules, ointments or creams which may be prepared in conventional manner.

Suitable daily dosages of the active compounds of general formula (I) whether administered internally or externally are generally in the range from 50 to 600 mg per man per day, depending upon the symptoms of the patient.

The compositions are preferably presented in the form of dosage units, each dosage unit being adapted to provide a fixed dose of active ingredient. Such compositions preferably contain from 25 to 100 mg of active ingredient per dosage unit.

Compositions in the form of tablets may be formulated with suitable amounts of various other ingredients such as, for example, excipients (e.g. lactose, glucose, sucrose or mannitol), disintegration agents (e.g. starch, sodium alginate, calcium carboxy-methyl-cellulose (CMC), crystal cellulose or sugar ester), lubricants (e.g. magnesium stearate or talc) and binding agents (e.g. simple syrup, gelatine solution, polyvinyl alcohol or polyvinylpyrrolidone). All of the abovementioned ingredients are used in the amounts conventionally used in the preparation of tablets. Dispersants (e.g. methylcellulose) and plasticizers may be used as coating agents for tablets.

Compositions according to the present invention presented in forms other than tablets and capsules, e.g. powders, preferably contain the active compounds of general formula (I) in amounts of from 5–10% by weight of the composition, together with other ingredients, generally excipients, e.g. lactose, glucose, sucrose and mannitol.

The acute toxicity, antiphlogistic and analgesic activities and the effect on gastric mucosa of 3-methyl-2-benzo(b) furylacetic acid and certain of the 5-substituted derivatives of general formula (I) according to the invention have been examined as described hereinafter. In the tests, the specimens Nos. 1–8 are the active compounds represented by the formula (I) according to the present invention and the specimens Nos. 9 and 10 are known compounds having known antiphlogistic and analgesic activities included for comparison purposes.

(I) Acute toxicity (determined as $LD_{50}$)

In this test, five groups, each consisting of 5 mice (male dd strain; weight: 19–21 g) and 5 rats (male Wistar strain; weight: 100–120 g) were used. Graded doses of the test compounds shown in Table I were administered orally to the test animals which were observed for one week. The $LD_{50}$ was calculated according to the method of Litchfield and Wilcoxon [Journal of Pharmacol. and Exper. Therap. 96, 99 (1949)]. The results obtained are shown in Table 1.

TABLE 1

| | Test Compound | Acute Toxicity (P.O.) Mouse | Rat |
|---|---|---|---|
| 1. | 3-methyl-2-benzo(b)furylacetic acid | >1100 | >300 |
| 2. | 5-chloro-3-methyl-2-benzo(b)furylacetic acid | 800 | 425 |
| 3. | 5-methoxy-3-methyl-2-benzo(b)furylacetic acid | 1108 | >1000 |
| 4. | 3,5-dimethyl-2-benzo(b)furylacetic acid | 1308 | >1000 |
| 5. | 5-fluoro-3-methyl-2-benzo(b)furylacetic acid | 1750 | >1000 |
| 6. | 5-tert-butyl-3-methyl-2-benzo(b)furylacetic acid | >1000 | >300 |
| 7. | 5-phenyl-3-methyl-2-benzo(b)furylacetic acid | 500–1000 | >300 |
| 8. | 5-benzyl-3-methyl-2-benzo(b)furylacetic acid | 500–1000 | >300 |
| 9. | 5-cyclohexyl-3-methyl-2-benzo(b)furylacetic acid | >1000 | >150 |
| 10. | Phenylbutazone | 860 | 620 |
| 11. | Ibuprofen | 1025 | 1400 |

(II) Anti-edema effect on carrageenin-induced edema on the hind paws of rats

The anti-edema effect was determined according to the method of Yamazaki et al [Yamazaki, H., et al; Folia Pharmacologica Japonica, 63, 302 (1967)].

In this test, a group consisting of five rats (male Wistar strain: weight 100–120 g) was used for the test and control groups. The compounds shown in Table 2 were administered orally to the rats of the test group. After one hour, 0.1 ml of a 1% carrageenin solution (phlogistic agent) was further administered to each rat by subcutaneous injection in one hind paw. To each rat of the control group, 0.1 ml of a 1% carrageenin solution was also administered in a similar manner to that for test rats. 1, 3 and 5 hours after administration of the phlogistic agent, the swelling ratio was calculated by means of the following equation:

Test group $$b = [(B' - B)/B] \times 100$$

in which b: swelling ratio
 B: volume of a hind paw without administration of phlogistic agent
 B': volume of a hind paw administered with phlogistic agent Control group $$a = [(A' - A)/A] \times 100$$

in which a: swelling ratio
 A: volume of a hind paw without administration of phlogistic agent
 A': volume of a hind paw administered with phlogistic agent The anti-edema effect was expressed as the suppression ratio of the edema in comparison with the control group to which the test compound had not been administered. The suppression ratio of the edema was determined 3 hours after administration of the phlogistic agent and was calculated by means of the following equation:

Suppression ratio = $a - b/a \times 100$ in which $a$ and $b$ are as hereinbefore defined. The results obtained are shown in Table 2.

TABLE 2

Anti-edema Effect
(Carrageenin Edema Method)
(Suppression Ratio - %)

| Test Compound | Amount of Administration | | | $ED_{50}$ mg/kg |
|---|---|---|---|---|
| | 75 mg/kg | 150 mg/kg | 300 mg/kg | |
| 1 | 25.3 | 41.2 | 54.2 | 240 |
| 2 | 45.7 | 63.3 | 74.2 | 880 |
| 3 | 34.5 | 60.8 | 73.1 | 110 |
| 4 | 43.8 | 56.2 | 70.9 | 100 |
| 5 | 37.0 | 60.0 | 71.9 | 105 |
| 6 | — | 39.9 | — | — |
| 7 | 52.7 | 63.9 | 73.3 | 70 |
| 8 | — | 31.1 | — | — |
| 9 | — | 28.0 | — | — |
| 10 | 42.6 | 53.5 | — | — |
| 11 | — | 45.3 | — | — |

Note: Test Compound -
1. 3-methyl-2-benzo(b)furylacetic acid
2. 5-chloro-3-methyl-2-benzo(b)furylacetic acid
3. 5-methoxy-3-methyl-2-benzo(b)furylacetic acid
4. 3,5-dimethyl-2-benzo(b)furylacetic acid
5. 5-fluoro-3-methyl-2-benzo(b)furylacetic acid
6. 5-tert-butyl-3-methyl-2-benzo(b)furylacetic acid
7. 5-phenyl-3-methyl-2-benzo(b)furylacetic acid
8. 5-benzyl-3-methyl-2-benzo(b)furylacetic acid
9. 5-cyclohexyl-3-methyl-2-benzo(b)furylacetic acid
10. Phenylbutazone
11. Ibuprofen
*100 mg/kg
**200 mg/kg (III) Analgesic activity in mice In this test, three groups, each consisting of 10 mice (male dd-strain; weight: 19–21 g) were used. The compounds shown in Table 3 were administered orally to the test mice. One hour after the administration, the mice were treated with 0.1 ml/10 g of 0.7% acetic acid solution in physiological saline by intraperitoneal injection according to the method of Koster et al [Koster, R., et al; Fed. Proc., 18, 412 (1959)]. Ten minutes after the treatment, the number of writhing reactions occurring in the mice was counted. Table 3 shows the analgesic effect expressed as the suppression ratio by comparison with the control mice which were not treated with the test compounds.

TABLE 3

Analgesic Effect
(AcOH Writhing Method)
(Suppression Ratio %)

| Test Compound | Amount Administered | | | $ED_{50}$ mg/kg |
|---|---|---|---|---|
| | 75 mg/kg | 150 mg/kg | 300 mg/kg | |
| 1 | 21.7 | 42.9 | 70.9 | 170 |
| 2 | — | 35.9 | 68.8 | 190 |
| 3 | — | 20.8 | 53.6 | 280 |
| 4 | — | 11.2 | 41.4 | 350 |
| 5 | — | 26.0 | 41.4 | 380 |
| 6 | — | 23.7 | — | — |
| 7 | — | 20.9 | 77.6 | — |
| 8 | — | 30.5 | 55.6 | — |
| 9 | 20.8* | 28.2** | — | — |
| 10 | — | 57.2 | — | — |

Note: Test Compound -
1. 3-methyl-2-benzo(b)furylacetic acid
2. 5-chloro-3-methyl-2-benzo(b)furylacetic acid
3. 5-methoxy-3-methyl-2-benzo(b)furylacetic acid
4. 3,5-dimethyl-2-benzo(b)furylacetic acid
5. 5-fluoro-3-methyl-2-benzo(b)furylacetic acid
6. 5-tert-butyl-3-methyl-2-benzo(b)furylacetic acid
7. 5-phenyl-3-methyl-2-benzo(b)furylacetic acid
8. 5-benzyl-3-methyl-2-benzo(b)furylacetic acid
9. Phenylbutazone
10. Ibuprofen
*100 mg/kg
**200 mg/kg (IV) Analgesic activity in rats A group consisting of 6–7 rats (male Wister strain; weight: 100–120 g) was used for the test and control groups in this test. Each rat of both groups was treated with 0.1 ml of a 1% carrageenin solution as phlogistic agent by subcutaneous injection in one hind paw. Three hours after the administration, pressure was applied to the treated paw of each rat by means of a pressing device (manufactured by Ugobasile S.A., Italy). The threshold of pain induced by press was measured with reference to the shriek and struggle according to the method of Randall and Selitto [Randall, L. O. and Selitto, J. J.; Arch, Int. Pharmocodyn., 111, 409 (1957)]. From each group 5 rats having a good response reaction, i.e. the pain threshold was not more than 70 g, were respectively selected. The active compound (each 150 mg/kg) shown in Table 4 were administered orally to the selected 5 test rats. 1, 2 and 3 hours after administration, pressure was again applied to both the inflamed and not inflamed paws of the test rats and the pain threshold was measured. On the other hand, without the administration of the active compound, the pressure was applied to both the inflamed and not inflamed paws of the selected 5 rats of the control group and the pain threshold was measured. The inflamed paws of the test and control groups were compared with each other. Also the not inflamed paws of the both groups were compared with each other.

The analgesic coefficient was calculated by means of the following equation, and the larger analgesic coefficient the better analgesic activity.

$$X = \frac{P_1 - P_2}{200 - P_2} \times 100 \, (\%)$$

in which X: analgesic coefficient (%)
$P_1$: threshold (g) of the test rats administered with active compounds
$P_2$: threshold (g) of the control rats without administration of active compound The results obtained are shown in Table 4.

TABLE 4

Analgesic Effect
(Randall-Selitto Method)

| Test Compound | | Analgesic Coefficient | | |
|---|---|---|---|---|
| | | 1 hr. | 2 hr. | 3 hr. |
| 1. | 3-methyl-2-benzo(b)furylacetic acid | 13.8 | 5.9 | 4.2 |
| | | 0.4 | 1.7 | 0 |
| 2. | 5-chloro-3-methyl-2-benzo(b)furylacetic acid | 25.1 | 17.8 | 16.3 |
| | | 0.5 | 1.3 | 2.4 |

TABLE 4-continued

Analgesic Effect
(Randall-Selitto Method)

| | Test Compound | Analgesic Coefficient | | |
|---|---|---|---|---|
| | | 1 hr. | 2 hr. | 3 hr. |
| 3. | 5-methoxy-3-methyl-2-benzo(b)furylacetic acid | 24.1<br>1.9 | 5.2<br>0 | 0<br>0 |
| 4. | 3,5-dimethyl-2-benzo(b)furylacetic acid | 35.4<br>0 | 18.8<br>0 | 7.1<br>0 |
| 5. | 5-fluoro-3-methyl-2-benzo(b)furylacetic acid | 38.6<br>0 | 23.5<br>0 | 19.3<br>0 |
| 6. | 5-tert-butyl-3-methyl-2-benzo(b)furylacetic acid | 19.5<br>6.0 | 17.8<br>0.8 | 14.4<br>1.3 |
| 7. | 5-phenyl-3-methyl-2-benzo(b)furylacetic acid | 37.2<br>8.0 | 23.3<br>2.4 | 11.3<br>4.7 |
| 8. | 5-benzyl-3-methyl-2-benzo(b)furylacetic acid | 23.1<br>1.7 | 24.7<br>0.7 | 29.5<br>6.1 |
| 9. | 5-cyclohexyl-3-methyl-2-benzo(b)furylacetic acid | 0<br>0 | 2.0<br>0 | 32.0<br>17.2 |
| 10. | Phenylbutazone | 20.7<br>3.8 | 23.2<br>5.4 | 27.7**<br>2.0 |
| 11. | Ibuprofen | 20.9<br>0.5 | 28.8<br>5.5 | 23.3<br>4.2 |

Note: Rat - (P.O.) 150 mg/kg
upper - inflamed paw
lower - not inflamed paw
**100 mg/kg (V) Effect on gastric mucosa The effect on gastric mucosa was determined according to the method of Hitchen et al [Hitchen et al: Pharmacologist, 19, 242 (1967)].

A test group consisting of 10–15 rats (male Wistar strain; weight: 180–220 g) was used in this test. Each rat was fasted for 20 hours, but water was allowed ad libitum. The compounds shown in Table 5 were administered orally. After a 20-hour interval during which the rats were not fed but were allowed water, each rat was administered under ether anesthesia with 0.5 ml per 100 g body weight of a 5% solution of pontamine sky blue 6BX in saline (pH 7.2 — adjusted with 0.5N HCl) by intravenous injection. 15 minutes after administration each rat was killed. The stomach was removed and maintained in a 1% formalin solution. After about 2 hours, the stomach was opened along the greater curvature and the length of lesions (dark blue areas against pale blue background) in the glandular portion was measured under a dissecting microscope (10X) provided with a square grid. The sum of the lengths (mm) of lesions was used as ulcer index. The compounds having an ulcer index of 5.0 or more had an ulcerogenic activity.

The dose level of the compound administered to the rats inducing gastric ulcers in 50% of the rats with an ulcer index of more than 5 is shown as $ED_{50}$ in Table 5.

TABLE 5

| Compounds | Ulcerogenic activity $ED_{50}$ (mg/kg P.O.) |
|---|---|
| 5-chloro-3-methyl 2-benzo(b)furylacetic acid | 230 |
| 5-methoxy-3-methyl 2-benzo(b)furylacetic acid | >300 |
| 3,5-dimethyl-2-benzo(b)furyl acetic acid | >300 |
| 5-fluoro-3-methyl 2-benzo(b)furylacetic acid | >300 |
| Phenylbutazone | 76 |
| Ibuprofen | 46 |

From the results shown it can be seen that the compounds according to this invention which were tested were superior to known non-steroidal antiphlogistic and analgesic agents such as phenylbutazone and ibuprofen.

The following Examples serves to illustrate the present invention. Examples 1 to 5 illustrate the preparation of the new compounds according to the invention, Examples 6 to 8 the preparation of the three previously known compounds, and Examples 9 to 12 the formulation of pharmaceutical compositions according to the invention.

EXAMPLE 1.

6.03 g of 5-methoxy-3-methyl-2-cyanomethylbenzo(b)furan were added to 100 ml of a 10% aqueous solution of sodium hydroxide and the mixture was heated under reflux for 10 hours. The reaction solution was then treated with active charcoal at an elevated temperature for decolorization and was then filtered. The pH of the filtrate was adjusted to 2 with concentrated hydrochloric acid (41.5 ml) and the filtrate was then cooled, whereupon crude crystals separated out. The crude crystals were collected and were then recrystallized from benzene to yield 3.76 g (56% yield) of 5-methoxy-3-methyl-2-benzo(b)furylacetic acid. The product had the following properties;

Melting point: 113°–114° C.
Elementary analysis: Calculated for $C_{12}H_{12}O_4$: C - 65.44, H - 5.49 (%). Found: C - 65.83, H - 5.72 (%).

EXAMPLE 2

5-Phenyl-3-methyl-2-benzo(b)furylacetic acid was prepared from 5-phenyl-3-methyl-2-cyanomethylbenzo(b)furan analogously to Example 1. Yield of purified product: 40%. The product had the following properties:

Melting point: 173°–174° C.
Elementary analysis: Calculated for $C_{17}H_{14}O_3$: C - 76.68, H - 5.30 (%). Found: C - 76.82, H - 5.22 (%).

EXAMPLE 3

5-Fluoro-3-methyl-2-benzo(b)furylacetic acid was prepared from 5-fluoro-3-methyl-2-cyanomethyl(b)furan analogously to Example 1. Yield of purified product: 56%. The product had the following properties:

Melting point: 129°–130° C.
Elementary analysis: Calculated for $C_{11}H_9O_3F$: C - 63.46, H - 4.36, F - 9.13 (%). Found: C - 63.82, H - 4.17, F - 9.24 (%).

EXAMPLE 4

5-Tert-butyl-3-methyl-2-benzo(b)furylacetic acid was prepared from 5-tert-butyl-3-methyl-2-cyanomethyl(b)furan analogously to Example 1. The product had the following properties:

Melting point: 169°–170° C.
Elementary analysis: Calculated for $C_{15}H_{18}O_3$: C - 73.14, H - 7.37 (%). Found: C - 72.98, H - 7.40 (%).

EXAMPLE 5

5-Benzyl-3-methyl-2-benzo(b)furylacetic acid was prepared from 5-benzyl-3-methyl-2-cyanomethyl(b)furan analogously to Example 1. The product had the following properties:

Melting point: 149°–150° C.
Elementary analysis: Calculated for $C_{18}H_{16}O_3$: C - 77.12, H - 5.75 (%). Found: C - 77.44, H - 5.68 (%).

EXAMPLE 6

5-Chloro-3-methyl-2-benzo(b)furylacetic acid was prepared from 5-chloro-3-methyl-2-cyanomethylbenzo(b)furan analogously to Example 1. The crude product was recrystallized from methanol-water (85:15 by volume). Yield: 63%. The purified product had the following properties:

Melting point: 149°–150° C.

Elementary analysis: Calculated for $C_{11}H_9O_3Cl$: C - 58.81, H - 4.04, Cl - 15.78 (%). Found: C - 58.61, H - 4.10, Cl - 15.59 (%).

EXAMPLE 7

3-Methyl-2-benzo(b)furylacetic acid was prepared from 3-methyl-2-cyanomethyl(b)furan analogously to Example 1. Yield of purified product: 40%. The product had the following properties:

Melting point: 108° C.

Elementary analysis: Calculated for $C_{11}H_{10}O_3$: C - 69.46, H - 5.30 (%). Found: C - 69.56, H - 5.39 (%).

EXAMPLE 8

3,5-Dimethyl-2-benzo(b)furylacetic acid was prepared from 3,5-dimethyl-2-cyanomethyl(b)furan analogously to Example 1. Yield of purified product: 50%. The product had the following properties:

Melting point: 116°–117° C.

Elementary analysis: Calculated for $C_{12}H_{12}O_3$: C - 70.57, H - 5.92 (%). Found: C - 70.29, H - 6.15 (%).

EXAMPLE 9

11.8 G of 5-cyclohexyl-3-methyl-2-acetylbenzo(b)furan and 2.2 g of sulphur were added to 6.0 g of anhydrous morpholin and the reaction mixture was heated under reflux for 15 hours. After the completion of the reaction, 60 ml of ethanol was added to the reaction mixture at 100° C. to obtain the precipitate of the thiomorpholide which were collected by filtration.

The crystals were allowed to hydrolyze at about 85° C. for 4 hours in the presence of 20 g of sodium hydroxide dissolved in 173 ml of 50% ethanol water (volume ratio).

After the completion of the reaction 3 l of water was added to the reaction mixture, followed by washing with 200 ml of benzene. The reaction solution was adjusted to an acidic pH 1.8 with 48 ml of conc. hydrochloric acid so as to isolate the desired acid, which was then filtered. The crystals were dispersed in 3 L of water and then 3.8 g of sodium bicarbonate was added to the dispersed solution.

After the crystal dispersed were dissolved by heating the solution, the solution was treated with active carbon. The decolored solution was adjusted to an acidic pH 1.9 with 4 ml of conc. hydrochloric acid so as to isolate the desired acid, which was then filtered. The crystals were recrystalized with 100 ml of benzene to obtain 10.6 g of 5-cyclohexyl-3-methyl-2-benzo(b)furylacetic acid with a yield of 84.3%.

The final product had the following properties:

Melting Point: 189°–190° C.

| Elemental Analysis | C (%) | H (%) |
|---|---|---|
| Calculated as $C_{17}H_{20}O_3$ | 74.97 | 7.40 |
| Found | 75.13 | 7.62 |

EXAMPLE 10

8.3 G of 5-fluoro-3-methyl-2-acetylbenzo(b)furan and 1.92 g of sulphur were added to 5.6 g of anhydrous morpholin and the reaction mixture was heated under reflux for 15 hours. After the completion of the reaction, the reaction mixture was concentrated under reduced pressure and 20 ml of water was added to the residue to give crude crystals which were collected by filtration. The crystals were allowed to hydrolyze at about 100° C. for 6 hours in the presence of 20 ml of acetic acid, 3.6 ml of concentrated sulfuric acid and 5.3 ml of water. The reaction solution was cooled and neutralized with aqueous sodium carbonate, followed by washing with benzene. The water layer of the reaction solution was adjusted to an acidic pH (2) with a suitable amount of hydrochloric acid so as to isolate the desired acid, which was then extracted with ethyl acetate. The ethyl acetate layer was treated with drying agent, Glauber's salt, and was concentrated. The residuum was recrystalized by using a 85% aqueous methanol to obtain 5.1 g of 5-fluoro-3-methyl-2-benzo(b)furylacetic acid with a yield of 56.2%. The final product had the following properties:

Melting point: 129°–130° C.

| Elemental analysis: | C (%) | H (%) | F (%) |
|---|---|---|---|
| Calculated as $C_{11}H_9O_3F$ | 63.46 | 4.36 | 9.13 |
| Found | 63.68 | 4.22 | 9.20 |

EXAMPLE 11

8.32 g (0.04 mole) of 5-fluoro-3-methyl-2-benzo(b)furylacetic acid was dissolved in 50 ml of water containing 1.6 g (0.04 mole) of sodium hydroxide. The solution was concentrated to 20 ml under reduced pressure, followed by adding 70 ml of methanol. The solution was filtered and then 500 ml of acetone was added dropwise to the filtrate to precipitate the crystals of Na-salt. 4.5 g of sodium salt of 5-fluoro-3-methyl-2-benzo(b)furylacetic acid was obtained after filtration and drying with a yield of 48.8%. The sodium salt had the following properties:

Melting Point: 300° C. up

| Elemental analysis: | C | H | F | Na |
|---|---|---|---|---|
| Calculated as $C_{11}H_8O_3FNa$ | 57.40 | 3.50 | 8.25 | 9.99 |
| Found | 57.59 | 3.63 | 8.31 | 9.86 |

EXAMPLE 12

Tablets are prepared in conventional manner from the following components:

| | mg/tablet |
|---|---|
| 5-chloro-3-methyl-2-benzo(b)furylacetic acid | 25.0 |
| Lactose | 19.3 |
| Carboxymethylcellulose (CMC) (as calcium salt) | 9.3 |
| Magnesium stearate | 0.4 |
| Talc | 0.8 |
| Polyvinylalcohol | 2.5 |
| Methylcellulose | 2.5 |
| Glycerine | 0.2 |
| Tar pigment | Trace |

EXAMPLE 13

Capsules are prepared in conventional manner from the following components:

| | mg/capsule |
|---|---|
| 5-methoxy-3-methyl-2-benzo(b)furylacetic | |

-continued

| | mg/capsule |
|---|---|
| acid | 50.00 |
| Cellulose (crystal) | 6.42 |
| Hydroxypropyl cellulose | 3.21 |
| Sucrose ester of aliphatic acid | 2.14 |
| Magnesium stearate | 6.45 |

EXAMPLE 14

A powder is prepared in conventional manner from the following components:

| | mg/1 g powder |
|---|---|
| 5-phenyl-3-methyl-2-benzo(b)-furylacetic acid | 50 |
| D-mannitol | 950 |

EXAMPLE 15

Tablets are prepared in conventional manner from the following components:

| | mg/tablet |
|---|---|
| 5-fluoro-3-methyl-2-benzo(b)-furylacetic acid | 100 |
| Lactose | 50 |
| Carboxymethylcellulose calcium salt | 5 |
| Polyvinylpyrrolidone | 4 |
| Calcium stearate | 1.5 |

EXAMPLE 16

Capsules are prepared in conventional manner from the following components:

| | mg/capsule |
|---|---|
| 5-phenyl-3-methyl-2-benzo(b)-furylacetic acid | 50 |
| Crystal cellulose | 20 |
| Magnesium stearate | 3.6 |
| Talc | 3.6 |

What is claimed is
1. A compound of the formula

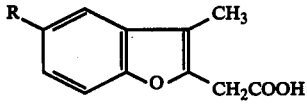

wherein R is a member of the group consisting of ethyl, n-propyl, isopropyl, n-butyl, sec-butyl or tert-butyl; and physiologically acceptable salts thereof.

2. A compound selected from the group consisting of 5-tert-butyl-3-methyl-2-benzo(b)furylacetic acid and a physiologically acceptable salt thereof.

3. A compound selected from the group consisting of 5-phenyl-3-methyl-2-benzo(b)furylacetic acid and a physiologically acceptable salt thereof.

4. A compound selected from the group consisting of 5-benzyl-3-methyl-2-benzo(b)furylacetic acid and a physiologically acceptable salt thereof.

5. A compound selected from the group consisting of 5-cyclohexyl-3-methyl-2-benzo(b)furylacetic acid and a physiologically acceptable salt thereof.

* * * * *